United States Patent
Hu (10) Patent No.: US 10,393,702 B2
(45) Date of Patent: Aug. 27, 2019

(54) DEFECT PENETRATION ESTIMATE USING MAGNETIC FLUX IMAGE ENHANCEMENT

(71) Applicant: Weatherford Technology Holdings, LLC, Houston, TX (US)

(72) Inventor: David Guoyu Hu, Houston, TX (US)

(73) Assignee: Weatherford Technology Holdings, LLC, Houston, TX (US)

( * ) Notice: Subject to any disclaimer, the term of this patent is extended or adjusted under 35 U.S.C. 154(b) by 216 days.

(21) Appl. No.: 15/341,408

(22) Filed: Nov. 2, 2016

(65) Prior Publication Data
US 2018/0120259 A1   May 3, 2018

(51) Int. Cl.
*G01N 27/82* (2006.01)
*G01N 17/04* (2006.01)

(52) U.S. Cl.
CPC ............. *G01N 27/82* (2013.01); *G01N 17/04* (2013.01)

(58) Field of Classification Search
CPC .............................. G01N 27/82; G01N 17/04
See application file for complete search history.

(56) References Cited

U.S. PATENT DOCUMENTS

| | | | | |
|---|---|---|---|---|
| 4,704,580 A * | 11/1987 | Moake | ................... | G01N 27/82 324/227 |
| 2005/0122121 A1* | 6/2005 | Gilboe | ................... | G01N 17/04 324/700 |
| 2006/0271299 A1* | 11/2006 | Ward | ................... | E21B 43/127 702/6 |
| 2007/0222438 A1* | 9/2007 | Reeves | ................... | G01N 27/82 324/240 |
| 2008/0049997 A1* | 2/2008 | Chin | ................... | G09G 5/028 382/128 |
| 2008/0159619 A1* | 7/2008 | Suh | ................... | G01N 27/902 382/152 |
| 2009/0229362 A1* | 9/2009 | Tomar | ................... | G01N 21/88 73/592 |
| 2009/0268973 A1* | 10/2009 | Majewicz | ................... | G06T 5/40 382/237 |
| 2015/0316508 A1* | 11/2015 | Lee | ................... | G01N 27/83 324/229 |

(Continued)

OTHER PUBLICATIONS

Pimenova, Anastasiya V., et al., "Magnetic Flux Leakage Method: Large Scale Approximation," Math. Model. Nat. Phenom., vol. 10, 2015, 12 pages.

(Continued)

*Primary Examiner* — Huy Q Phan
*Assistant Examiner* — Zannatul Ferdous
(74) *Attorney, Agent, or Firm* — Lewis & Reese, PLLC (57) ABSTRACT

An improved process for evaluating a defect in wellbore casing using a magnetic flux leakage tool is disclosed. According to the disclosed technique, signals recorded using a magnetic flux leakage tool are arranged into a matrix that defines a magnetic flux leakage image, and a defect in the evaluated wellbore casing is identified in the image. A portion of the image in which the defect appears is enhanced using an iterative image enhancement process to determine a geometry of the defect. A characteristic value of the defect is then used in conjunction with a characteristic value-degree of penetration relationship that is specific to the determined geometry in order to determine the degree of penetration of the defect.

18 Claims, 7 Drawing Sheets

(56) References Cited

U.S. PATENT DOCUMENTS

2018/0098075 A1\* 4/2018 Sasai .................... H04N 19/197

OTHER PUBLICATIONS

Rutledge, Kory, Power-point presentation entitled "Casing Integrity Tools," Weatherford, Jan. 2015, 37 pages.

Sharar, M. A. et al., "High Resolution Casing Imaging Utilizing Magnetic Flux Leakage Measurements," SPWLA 49th Annual Logging Symposium, May 25-28, 2008, 10 pages, Edinburgh, Scotland.

\* cited by examiner

DEFECT PENETRATION ESTIMATE USING MAGNETIC FLUX IMAGE ENHANCEMENT

FIELD OF THE INVENTION

The present application relates to techniques for enhancing the resolution of magnetic flux leakage images. In particular, the application is directed to the use of resolution enhancement techniques to estimate the geometry of a defect with greater accuracy, which, in turn, enables the degree of penetration of the defect to be determined with greater accuracy.

BACKGROUND

Figure 1:
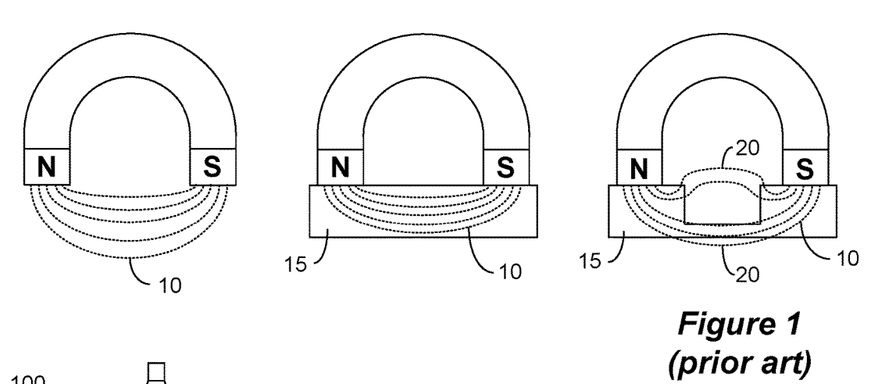
FIG. 1 illustrates the concept of magnetic flux leakage in accordance with the prior art.

As illustrated in FIG. 1, magnetic flux 10 travels between the poles of a magnetic field along a path of least reluctivity (i.e., highest permeability). When a ferromagnetic material 15 is present within a magnetic field, the magnetic flux 10 concentrates within the ferromagnetic material 15, which has a magnetic permeability that is much higher than non-ferromagnetic materials. However, the flux capacity of a ferromagnetic material 15 is proportional to its cross-sectional area. Therefore, when the cross-sectional area of a flux-carrying ferromagnetic material 15 is reduced, magnetic flux "leaks" 20 into the surrounding medium. This flux leakage 20 occurs on both sides of the ferromagnetic material 15.

Magnetic flux leakage (MFL) tools take advantage of this phenomenon to identify and evaluate defects in oil and gas well casings. MFL tools induce a magnetic flux within the ferromagnetic (e.g., steel) wall of a casing and measure any changes in the magnetic flux that "leaks" from inside the casing wall. The MFL tool 100 illustrated in FIG. 2 includes a strong permanent magnet 105 (such as a Samarium-Cobalt magnet) that induces a magnetic flux that travels along the longitudinal axis of a wellbore, primarily within the wall of the casing. The MFL tool 100 additionally includes a plurality of pads 110 that are positioned around the circumference of the tool 100, each pad 110 biased towards the interior wall of the casing. Each pad includes one or more corrosion sensors that measure magnetic flux in the longitudinal direction (i.e., the flux generated as a result of the permanent magnet). Each pad 110 also includes one or more discriminator sensors that measure magnetic flux in a direction orthogonal to the longitudinal direction, which flux is induced by one or more smaller permanent magnets also positioned on the pad 110. The flux leakage measured by the discriminator sensors is more sensitive to defects in the interior wall of the casing. The MFL tool 100 additionally includes an upper centralizer 115 and a lower centralizer 120 that keep the MFL tool 100 positioned in the center of the casing.

Figure 2:
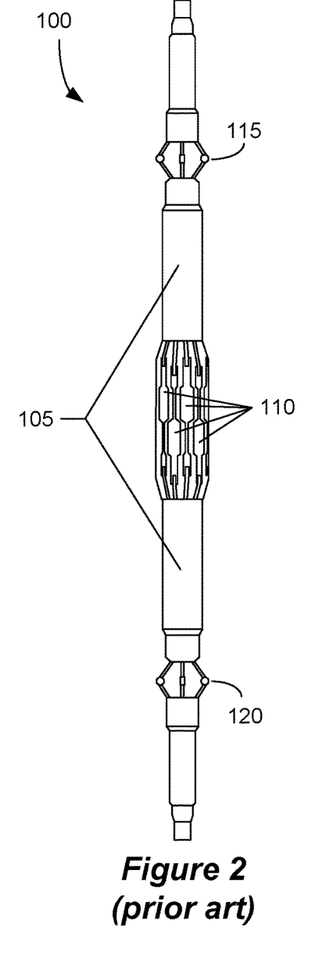
FIG. 2 illustrates an example magnetic flux leakage tool in accordance with the prior art.

The MFL tool 100 is specific to a particular range of casing sizes, and the number of pads 110 and corrosion sensors is dependent upon the specific tool. By way of example, the tool 100 may include between 10 and 16 pads and between 30 and 80 corrosion sensors, which corrosion sensors may be arranged in groups of three to five sensors per pad. These types of tools may service API casing having an external diameter between 4½ and 9⅝ inches. It will be understood that different MFL tools may include different numbers of pads and sensors and may service different casing sizes.

The corrosion and discriminator sensors generate an electrical signal that is proportional to the amount of flux traveling through the sensor in the selected direction (i.e., the longitudinal direction for corrosion sensors and orthogonal to the longitudinal direction for discriminator sensors). The sensors are typically Hall Effect sensors, but they can also be coil-type sensors. The electrical signal at each of the sensors is recorded periodically as the tool travels in the wellbore. Recording of the signals may be accomplished by storing digitized values of the signals in a memory contained within the tool 100 or by transmitting the values to a system at the surface such as via a wireline that conveys the tool 100 into the wellbore. The MFL tool 100 may be logged at a rate of 6000 feet per hour, and, at that rate, the signal from each of the tool's sensors may be recorded at a rate of 120 samples per foot, although other conveyance and recording rates may also be used.

Figure 3:
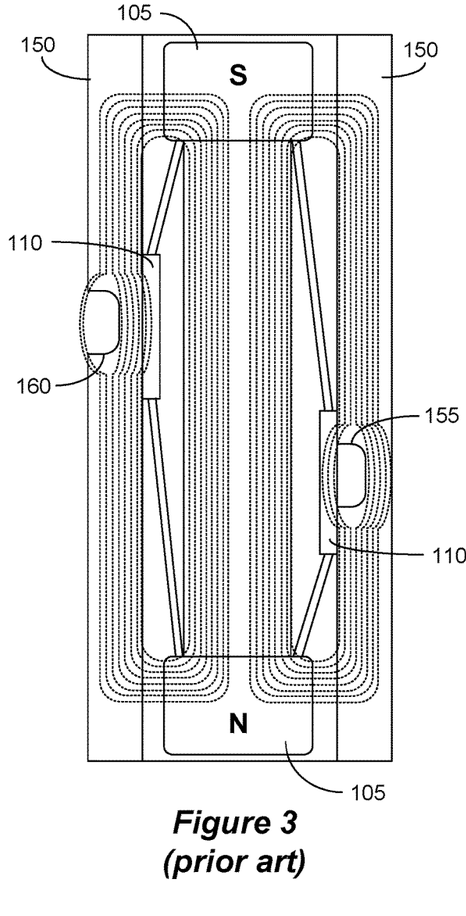
FIG. 3 illustrates a cross-sectional view of a portion of the MFL tool of FIG. 2 within a well casing in accordance with the prior art.

As illustrated in the cross-sectional schematic view in FIG. 3, the magnetic flux induced by the permanent magnet 105 in the tool travels primarily within the wall of the casing. The magnet 105 is typically sized for the specific type of casing such that the field strength results in near magnetic saturation of the casing wall 150. As shown in FIG. 3, magnetic flux leakage occurs on both sides of the casing wall 150 in the area of both internal defects 155 and external defects 160. The corrosion sensors, which are positioned on the pads 110 riding along the interior wall of the casing 150, will therefore measure increased magnetic flux in the area of either an internal defect 155 or an external defect 160. Because the magnets associated with the discriminator sensors are not strong enough to magnetize the full thickness of the wall 150, the discriminator sensors exhibit a greater response to internal defects 155. As such, the response measured by a corrosion sensor can be classified as corresponding to either an internal defect 155 or an external defect 160 based on the response of a closely-positioned discriminator sensor.

Figure 4:
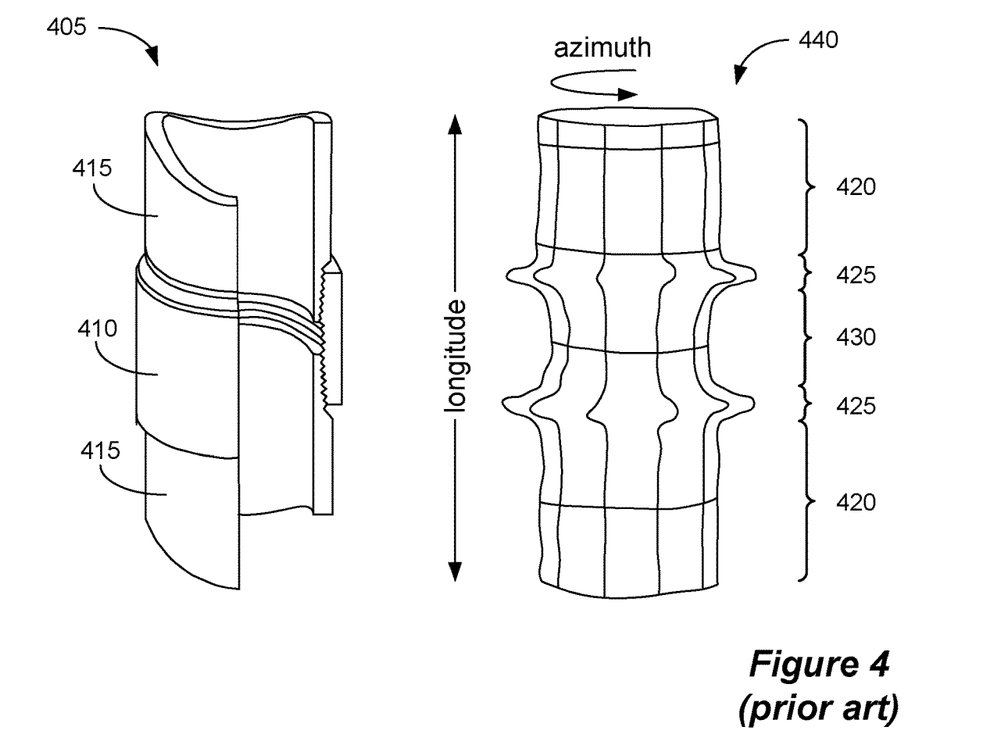
FIG. 4 illustrates a cutaway view of a coupling within a casing string and an associated MFL image compiled from MFL signals recorded by a MFL tool in accordance with the prior art.

Signals representative of magnetic flux are recorded from sensors positioned at numerous azimuthal positions at each of numerous longitudinal positions within the cased wellbore. These recorded signals can be compiled into a magnetic flux leakage image that provides a visualization of the features of the evaluated casing. FIG. 4 shows a cutaway view of section of a casing string 405 that includes a coupling 410 and an example of the MFL image 440 associated with the section of the casing string 405. The signals recorded from each of the corrosion sensors in regions 420 of defect-free casing 415 are substantially equal and correspond to the nominal flux for the casing type. In the regions 425 near the outer edges of the coupling 410, the signals recorded from each of the corrosion sensors are also substantially equal, but they correspond to a magnetic flux that is greater than the nominal flux. The increased flux leakage that is detected at all azimuthal positions in the regions 425 is due to the incomplete engagement of the casing's threads with the coupling's threads, which results in a decreased wall thickness at the initiation of the casing threads. In the region 430 corresponding to the coupling 410, the signals recorded from each of the corrosion sensors are still substantially equal, but they correspond to a magnetic flux that is less than the nominal flux. The decreased flux leakage that is detected at all azimuthal positions in this region is due to the increased wall thickness of the coupling 410 as compared to the wall thickness of the casing 415, which results in the additional concentration of magnetic flux within the wall of the coupling 410 and therefore decreased magnetic flux measured by the corrosion sensors.

Figure 5:
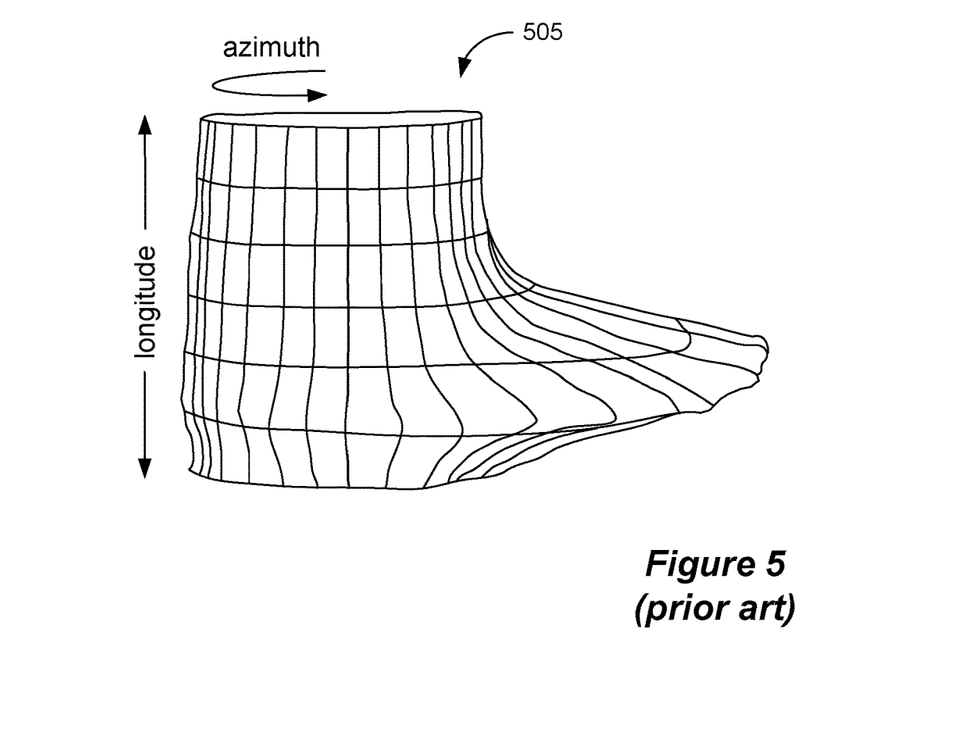
FIG. 5 illustrates an example MFL image corresponding to a defect within an evaluated casing string in accordance with the prior art.

The signals recorded by the MFL tool's sensors can also be utilized to visualize defects in the casing wall. The MFL image 505 in FIG. 5 visually depicts the magnetic flux measured in a region of casing having a defect. The corrosion sensors at azimuthal positions near the defect measure increased magnetic flux leakage as a result of the decreased wall thickness caused by the defect while corrosion sensors at other azimuthal positions measure magnetic flux corresponding to the nominal flux value. The image 505 enables a determination of the longitudinal and azimuthal location of a defect, but the magnetic flux signals recorded by the tool 100 can additionally be utilized to evaluate the degree of penetration of the defect and the burst pressure of the casing as a result of the defect.

Figure 6:
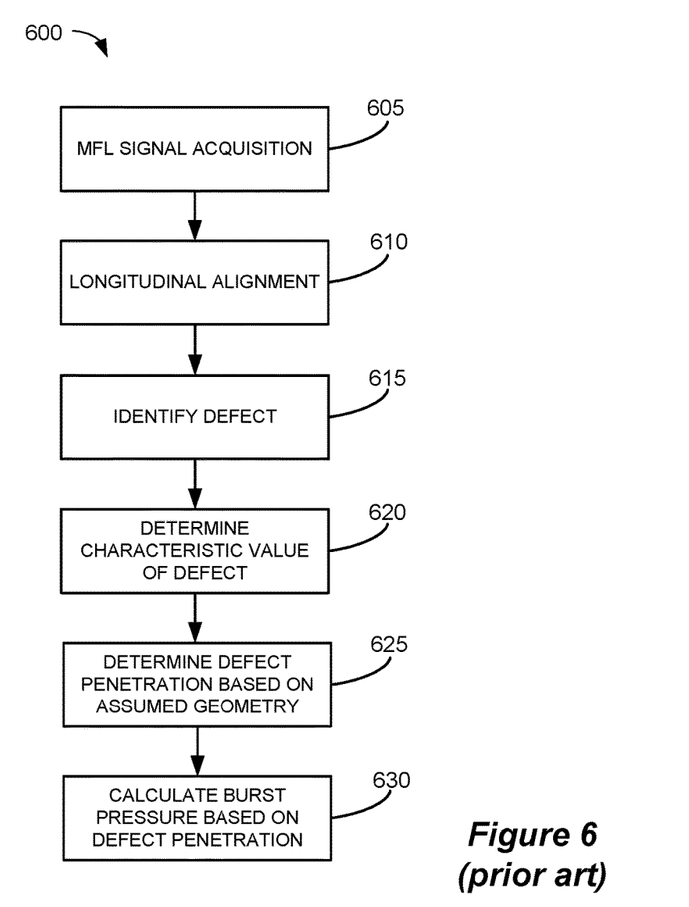
FIG. 6 illustrates a process for determining a degree of penetration of a casing defect and an associated burst pressure as a result of the defect in accordance with the prior art.

FIG. 6 illustrates an existing process 600 for determining the degree of penetration of a defect within an evaluated casing string and the casing string's burst pressure as a result of the defect. The MFL signals are acquired at step 605 as described above. The MFL signals may be acquired over a range of longitudinal positions within which there is believed to be a casing defect or may be acquired over a substantial length of the casing string as part of a routine analysis. As noted above, the MFL signals may be transmitted to the surface as they are acquired or they may be stored by the tool 100 and the recorded signals may be recovered when the tool 100 is subsequently brought to the surface. The acquired signals are then aligned to consistent longitudinal positions (step 610). Note from FIGS. 2 and 3 that the pads 110 are at different longitudinal positions. Moreover, the corrosion and discriminator sensors on a particular pad may also be at different longitudinal positions. Thus, signals acquired by the various sensors at the same point in time correspond to different longitudinal positions. At step 610, the signals are adjusted to a consistent longitudinal scale. The longitudinal alignment process arranges the recorded MFL signals into a matrix that defines an MFL image, where each value represents a single pixel in the image. Each column in the matrix includes MFL signals recorded by a single corrosion sensor at different longitudinal positions and each row in the matrix includes MFL signals recorded by the different corrosion sensors at a common longitudinal position.

At step 615, the aligned signals (i.e., the signals that make up the image) are evaluated to identify a casing defect through a quantitative analysis of the signals. A defect may be identified on the basis of the magnitude of the raw MFL signals or on the basis of some other quantitative metric such as a first or second order derivative of the MFL signals with respect to longitudinal position, for example. The identification of a defect may also involve the identification of a longitudinal range within which the defect is to be further evaluated. This, too, may be based upon a quantitative analysis of the MFL signals. Defect identification can also involve discarding regions of increased magnetic flux that do not correspond to a defect, such as the regions 425 in FIG. 4. This process can be performed through quantitative and/or qualitative analysis. At the defect identification stage, the defect is also classified as either internal or external. As described above, this determination is based upon the signals recorded by the discriminator sensors within the region of the defect.

Having identified a defect, a characteristic value of the defect is computed (step 620). Like the identification of a defect, the characteristic value of the defect can also be determined quantitatively from the MFL signal values. For example, the characteristic value of the defect may be the maximum raw value within the determined longitudinal range. In a particular example, the characteristic value is the maximum value of the second derivative with a selected longitudinal window length (i.e., a particular longitudinal distance over which signal change is evaluated) of the MFL signal values with respect to longitudinal position within the determined longitudinal range. The characteristic value can also be computed using other metrics that are relatable to the degree of penetration of the defect.

Figure 7:
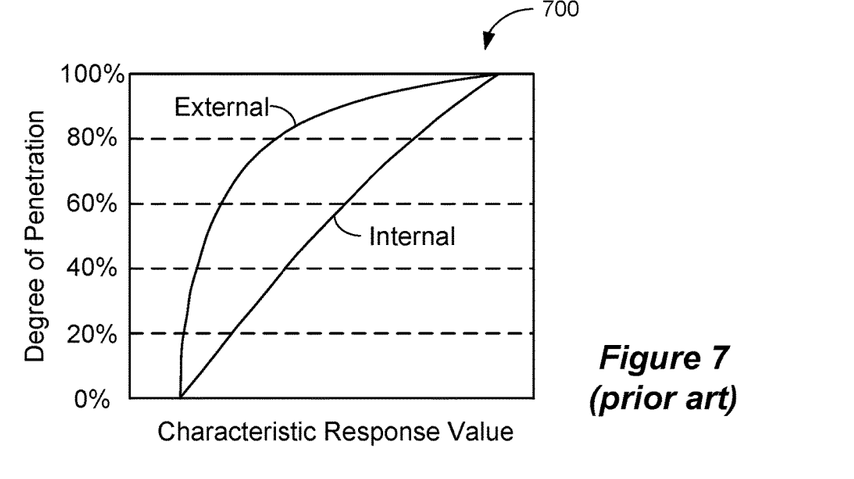
FIG. 7 illustrates a relationship between the characteristic value of a defect as determined from recorded MFL signals and the degree of penetration of the defect for an assumed defect geometry in accordance with the prior art.

The degree of penetration of the defect is determined based on the characteristic value of the defect and the defect's classification as either internal or external (step 625). FIG. 7 shows an example characteristic value-degree of penetration relationship 700 (hereinafter "relationship"). This type of relationship is developed experimentally by determining the characteristic value for known defects having different degrees of penetration and different classifications (i.e., internal or external origination). For example, the characteristic value may be determined for defects having degrees of penetration between 5% and 100% of the casing wall thickness in 5% increments for both internal and external detects. The relationship is specific to a particular type of MFL tool and a particular type of casing because different types of tools record different MFL signals for the same casing defect and different types of casing (i.e., different sizes, grades and wall thicknesses) result in different characteristic values for the same defect. The relationship is also based upon an assumed defect geometry as described below. Using the experimental data, the relationship can be expressed in the form of an equation (more specifically, an equation for internal defects and an equation for external defects) using linear or non-linear fitting techniques or as a lookup table. If the relationship is expressed in the form of an equation, the degree of penetration can be computed directly by solving for the degree of penetration using the known characteristic value. If the relationship is expressed as a lookup table, the degree of penetration can be determined as the value corresponding to the determined characteristic value in the lookup table or by interpolation if the determined characteristic value does not exist in the lookup table, The burst pressure of the casing can be calculated as a function of the outside diameter of the casing, the material strength of the casing, the wall thickness, and an applied safety factor using an equation such as Barlow's equation. The degree of penetration of the defect can be used to compute the remaining wall thickness at the defect (i.e., by subtracting the wall thickness removed as a result of the penetration of the defect from the known original wall thickness) in order to calculate the burst pressure of the casing as a result of the defect (step 630). As is known, the burst pressure provides an estimate of the fluid pressure that the casing can withstand before it ruptures. Thus, the calculated burst pressure is an important parameter to evaluate in considering the need for remedial action.

One downfall of the process 600 is that, because magnetic flux leakage is dependent upon both the degree of penetration of a defect as well as the defect's geometry, the relationship must be generated for an assumed defect geometry. For example, the relationship 700 may be constructed based upon recorded MFL signals for different degrees of penetration for a circular defect having a diameter equal to three times the thickness of the casing wall (i.e., a 3 T circular defect). Because the relationship is based upon an assumed geometry, the calculation of the degree of penetration can be incorrect if the actual defect has a geometry that deviates from the assumed geometry upon which the relationship is based. For example, the magnetic flux leakage for a 5 T circular defect is greater than the magnetic flux leakage for a 3 T circular defect of the same degree of penetration. Thus, the calculated characteristic value for a 5 T circular defect differs from the characteristic value for a 3 T circular defect of the same degree of penetration, so the calculated degree of penetration for the 5 T circular defect would differ from the actual degree of penetration due to the relationship's assumption of a 3 T circular defect.

Figures 8, 12:
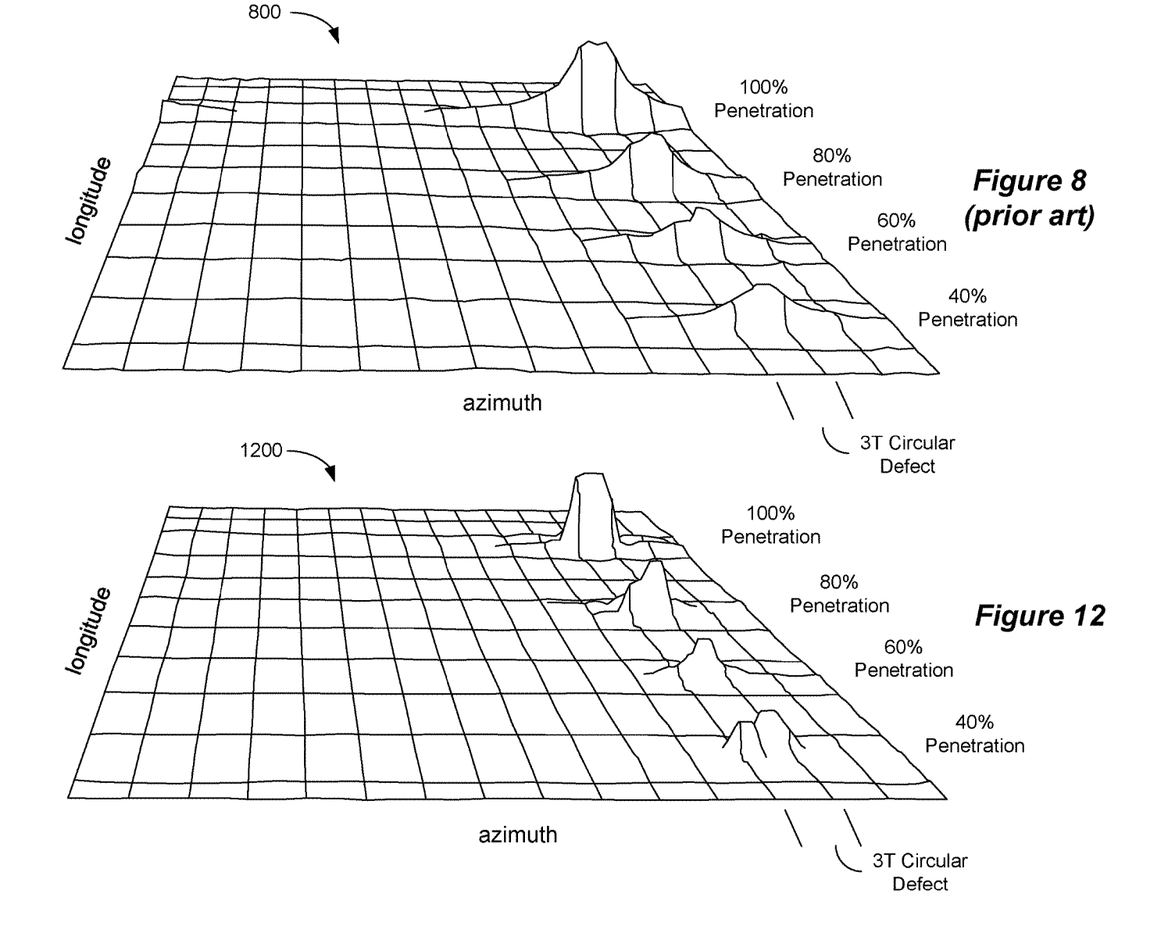
FIG. 8 illustrates an MFL image of defects having a common geometry and different degrees of penetration in accordance with the prior art.
FIG. 12 illustrates an enhanced MFL image of the defects in FIG. 8 in accordance with an aspect of the invention.

The geometry of a defect can be estimated based upon the longitudinal range over which magnetic flux leakage is recorded (the longitudinal dimension of the defect) and the number of corrosion sensors that record the magnetic flux leakage (the azimuthal dimension of the defect). Such estimates of the defect geometry can be utilized to adjust the characteristic value to account for a difference from the assumed geometry such that the relationship can be utilized to calculate the degree of penetration. However, it can be difficult to determine the geometry of a defect from the MFL response. FIG. 8 illustrates an MFL image 800 (presented in a planar orientation rather than the cylindrical orientation in FIGS. 3 and 4) that depicts 3 T circular internal defects having degrees of penetration of 100%, 80%, 60%, and 40%. While the depictions of the defects are generally sharp in the longitudinal direction (i.e., the defect's edges are easily identifiable in the longitudinal direction), they are blurry in the azimuthal direction (i.e., the defect's edges are not easily identifiable in the azimuthal direction). The difference in resolution in the longitudinal and azimuthal directions is primarily due to the longitudinal direction of the magnetic field induced by the MFL tool. The corrosion sensors measure a sharp change in the magnetic flux at the starting and ending longitudinal positions of a defect, but corrosion sensors well outside of the azimuthal region of the defect also measure a response to the defect, which results in the blurriness of the image in the azimuthal direction. Moreover, as illustrated in FIG. 8, the blurriness is exacerbated at increased degrees of penetration. This image blurriness can make it difficult to determine the geometry of a defect. For example, it can be difficult to determine whether a defect has an azimuthal dimension of 3 T and a higher degree of penetration or an azimuthal dimension of 5 T and a lower degree of penetration. Therefore, it can be difficult to adjust the characteristic value to account for differences in geometry from the geometry upon which the relationship is based. As a result, the calculated degree of penetration and burst pressure is susceptible to errors. The invention disclosed in this application provides an improved process for determining the geometry of a defect based on MFL signals collected by a tool such as the MFL tool 100, which enables greater accuracy in the determination of the degree of penetration of the defect and the associated burst pressure of the evaluated casing.

DETAILED DESCRIPTION OF THE INVENTION

Figure 9:
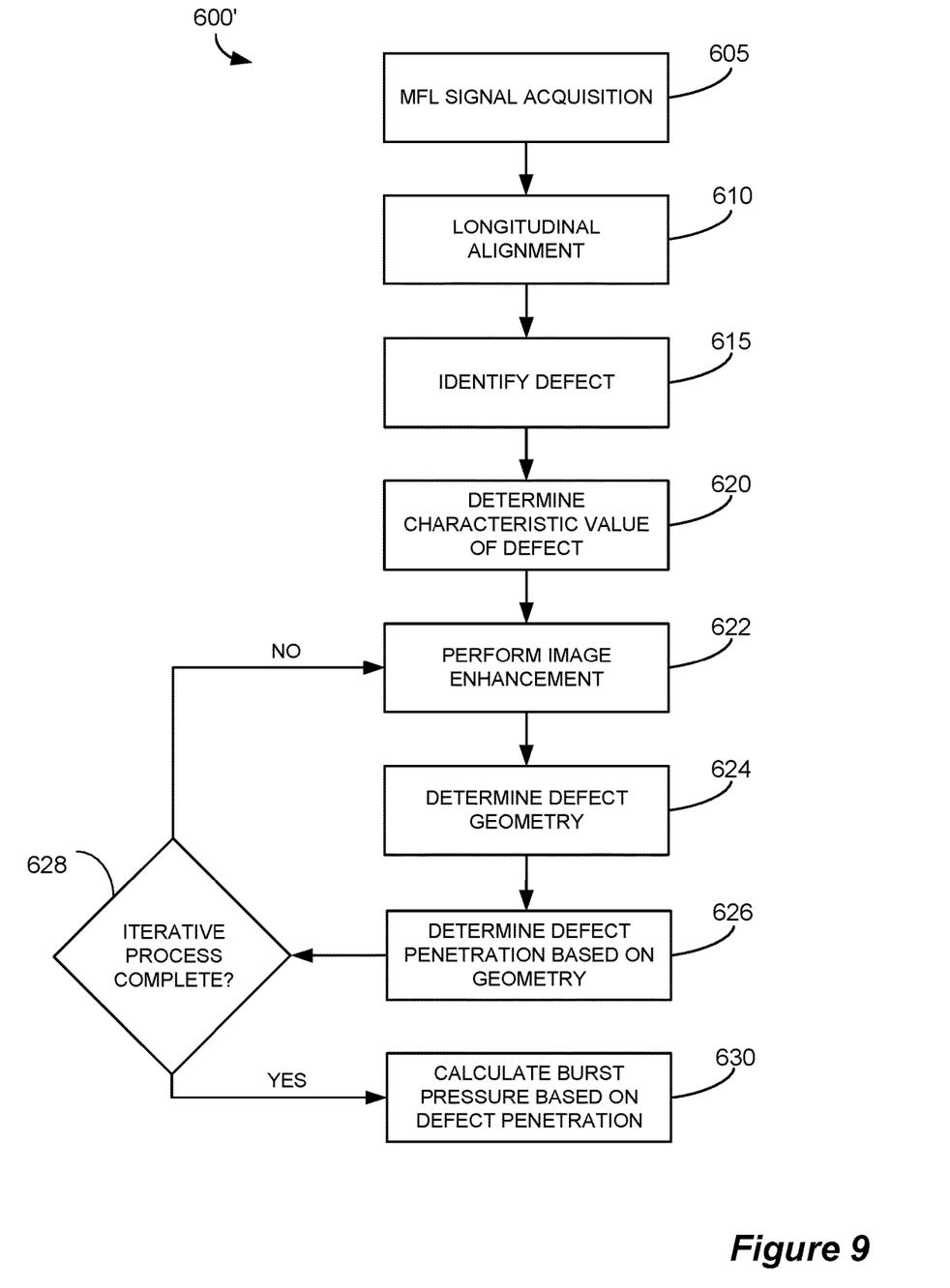
FIG. 9 illustrates an improved process for determining a degree of penetration of a casing defect and an associated burst pressure as a result of the defect using MFL image enhancement in accordance with an aspect of the invention.

FIG. 9 illustrates a modified process 600' for determining the degree of penetration of a casing defect and the corresponding burst pressure of the casing. The MFL signals are acquired and longitudinally aligned (steps 605 and 610) in the same manner as described above with respect to process 600. Likewise, a defect is identified and its characteristic value is determined (steps 615 and 620) in the same manner as described above with respect to the process 600. However, rather than determining the degree of penetration of the defect using a relationship that is based on an assumed geometry as in the process 600, an image enhancement process is performed (step 622). As described above, the recorded MFL signals are arranged during the longitudinal alignment step (step 610) into a matrix that defines an MFL image in which each recorded MFL signal represents a single pixel. A portion of the MFL image corresponding to a particular longitudinal range within which the defect appears is enhanced through the image enhancement process in step 622. The particular portion of the MFL image that is enhanced can be determined in different manners. For example, the longitudinal edges of the defect may be identified using known edge detection techniques and the portion may include a longitudinal range that is a fixed number of rows of pixels wider than the longitudinal dimension of the defect (e.g., from X rows of pixels above the top edge of the defect to X rows below the bottom edge of the defect). Similarly, the portion of the image that is enhanced may include a longitudinal range that is centered over the defect and that has a longitudinal dimension that is a predefined multiple of the defect's longitudinal dimension. Image enhancement is typically performed across the full azimuthal range within the selected longitudinal range, but the azimuthal range might be cropped as well.

The image enhancement technique applied to the selected portion of the MFL image is based upon a modified version of the Van Cittert deconvolution algorithm. The deconvolution algorithm is an iterative algorithm that operates to reverse the effects of convolution on the recorded MFL signals. In particular, the deconvolution algorithm acts to sharpen the selected portion of the MFL image in the azimuthal direction such that the edges of the defect are more easily identifiable.

Figure 10:
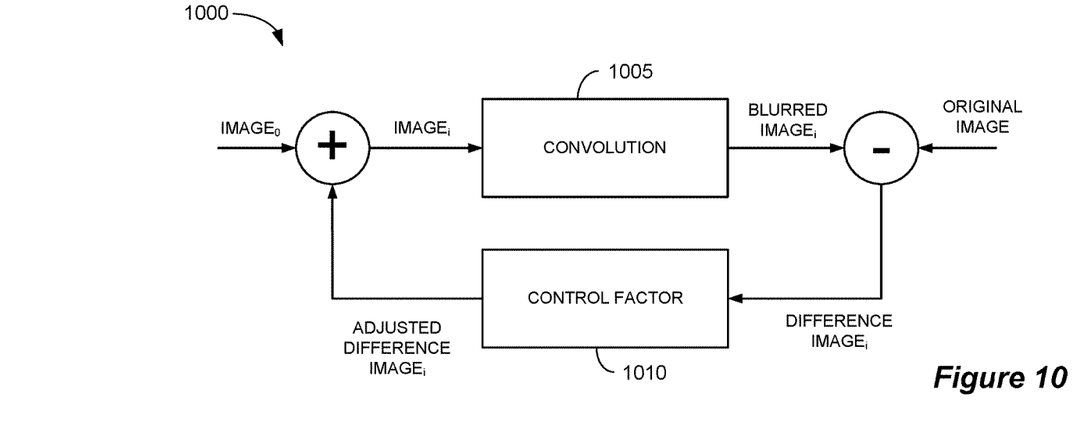
FIG. 10 illustrates a process flow diagram of an MFL image enhancement process in accordance with an aspect of the invention.
Figure 11:
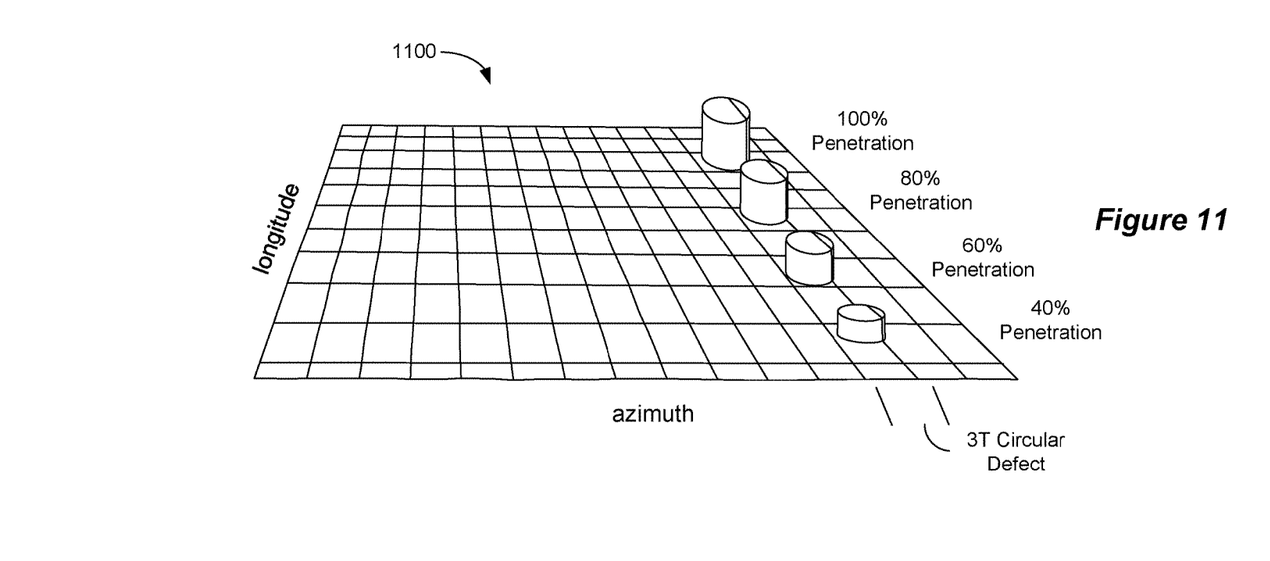
FIG. 11 illustrates an ideal MFL image of the defects in FIG. 8 in accordance with an aspect of the invention.

As illustrated in FIG. 10, the deconvolution algorithm 1000 begins with an initial estimate of the selected portion of the image (image$_0$). In the case of the process 600', this initial estimate is the selected portion of the recorded MFL image itself. In the first iteration of the deconvolution algorithm 1000, there is no difference image to be added to the image estimate, so the initial estimate is convolved 1005 by applying a system transfer function to the estimate. The system transfer function is an estimate of the manner in which the MFL tool convolves an ideal MFL response to a defect (i.e., a response having sharp edges in the azimuthal direction) to arrive at the actual, recorded response. For example, the transfer function seeks to mathematically describe the manner in which the ideal responses to the defects illustrated in FIG. 11 are convolved by the MFL tool to generate the responses in FIG. 8. The system transfer function is specific to the particular type of MFL tool and is dependent upon the geometry of the defect (including whether it is an internal or external defect) and its degree of penetration. Thus, for a particular MFL tool, there are actually multiple system transfer functions, each applying to a particular geometry and degree of penetration. The different system transfer functions can be determined experimentally by relating an MFL tool's recorded response to the ideal response for each of the desired defect geometries and degrees of penetration. While this can be accomplished through actual analysis of defects of different geometries and degrees of penetration, in a preferred embodiment, the MFL tool response to the different types of defects is estimated using finite element modeling. This approach enables the determination of the transfer function for practically any defect geometry and degree of penetration.

The system transfer function to be applied during a particular iteration is based on the then-current estimate of the defect geometry and the degree of penetration. For the initial iteration, these parameters can be determined in different ways. In a first embodiment, the system transfer function applied during the initial iteration is based on an assumed defect geometry and degree of penetration regardless of the characteristic value or the properties of the image. For example, the selected portion of the image may be convolved in the initial iteration using the transfer function associated with an internal 3 T circular defect with a 60% degree of penetration. In another embodiment, the geometry may be assumed for the initial iteration, but the degree of penetration of the defect may be determined based on the characteristic value (determined in step 620) using the relationship for the assumed geometry. For example, the geometry may be assumed to be an internal 3 T circular defect for the initial iteration, but the degree of penetration may be calculated based on the characteristic value using the internal 3 T circular relationship. In yet another embodiment, the geometry can be estimated from the initial image and the degree of penetration of the defect can be determined from the relationship for the estimated geometry. For example, the geometry can be estimated using known edge detection techniques such as Canny edge detection, or other first or second order edge detection techniques. As will be described in greater detail below, one of the benefits of the improved process 600' is that relationships exist for multiple defect geometries, so the degree of penetration can be determined using the relationship for the estimated geometry.

Regardless of the manner in which the initial system transfer function is selected, it is applied to convolve 1005 the initial image estimate (i.e., the selected portion of the image). The result of the convolution 1005 via the transfer function is a blurred image. The blurred image is then subtracted in a pixel-by-pixel manner from the original image (i.e., the selected portion of the original image) to obtain a difference image. Note that if the current image estimate represents the ideal MFL response to a particular defect, the blurred image is equal to the original image. Thus, the difference image represents the difference between the ideal MFL response and the current image estimate. A control factor may be applied 1010 to the difference image by multiplying each pixel in the difference image by the control factor to alter the effect of the difference image. If the control factor is set to a value of one, the adjusted difference image is equal to the difference image, but a value of less than or greater than one can be implemented to increase or decrease the effect of the difference image. The difference image (as adjusted by the control factor) is added to the current image estimate in a pixel-by-pixel manner to obtain an enhanced portion of the image, which enhanced portion is the estimate of the selected portion of the image in a succeeding iteration.

Referring back to FIG. 9, the new image estimate (i.e., the enhanced portion of the image, image$_i$) is utilized to determine the geometry of the defect (step 624). As described above, the defect geometry can be determined by identifying the edges of the defect in the image estimate using known edge detection algorithms. In one embodiment, the geometry may be expressed in terms of the defect's azimuthal and longitudinal dimensions, which dimensions may be determined, for example, as the maximum distance between the edges of the defect in the image estimate in the specified directions. This approach can be used to specify circular and elliptical-shaped defects. While the defect geometry may be expressed simply in terms of its azimuthal and longitudinal dimensions, the defect geometry may also be expressed in terms of more complex parameters based on the identified edges of the defect in the image estimate. For example, the defect geometry could also be specified in terms of multiple azimuthal and longitudinal dimensions.

The degree of penetration is determined from the relationship that corresponds to a geometry that is most closely related to the determined geometry. As briefly mentioned above, a beneficial aspect of the process 600' is that the degree of penetration is determined from a characteristic value-degree of penetration relationship that is specific to the determined geometry. The relationship for each of the different geometries can be expressed in the same manner as the relationship described above (e.g., as an equation or as a lookup table). Like the transfer functions, the relationships can be developed using finite element modeling, which enables the creation of relationships for practically any desired geometry. The degree of penetration can be determined based upon the characteristic value determined in step 620, or, alternatively, the characteristic value can be updated using the current image estimate, although the latter is obviously more computationally intensive. In another embodiment, the enhanced image can be scaled back in absolute values so that the characteristic value of the defect remains unchanged, which gives rise to better noise tolerance and stability. Such scaling-back can happen between iterations, and/or at the end of the last iteration.

After determining the defect geometry and the degree of penetration, it is determined whether the iterative process (i.e., the process defined by steps 622, 624, and 626) is complete (step 628). In a first embodiment, the iterative process can be determined to be complete when the number of iterations reaches a fixed iteration count. For example, the process 600' may include five iterations of steps 622 through 628 regardless of the results of the steps. In another embodiment, the iterative process can be determined to be complete based upon a convergence test. Such a convergence test may evaluate different parameters such as the difference image or the degree of penetration to determine whether the parameters have converged. In yet another embodiment, the iterative process can be determined to be complete based upon a combination of a fixed iteration count and a convergence test. For example, the iteration completion may be accomplished upon the first of either a set number of iterations or the satisfaction of a convergence test.

If it is determined that the iterative process is not complete (the "No" prong of step 628), image enhancement (step 622) is repeated. Image enhancement for iterations subsequent to the first iteration begins with the image estimate from the previous iteration (i.e., image$_i$). The system transfer function to be applied to the image estimate during iterations subsequent to the first iteration is selected based upon the defect geometry and the degree of penetration of the defect as determined in steps 624 and 626 (i.e., as determined during the preceding iteration). If it is determined that the iterative process is complete (the "Yes" prong of step 628), the burst pressure of the casing is calculated based upon the degree of penetration of the defect in the same manner as described above with respect to process 600 (step 630).

FIG. 12 illustrates the effect of the application of the image enhancement process 1000 to the initial recorded images of FIG. 8. As can be seen, the edges of the defects in the azimuthal direction reflect a common azimuthal dimension regardless of the degree of penetration. From these enhanced images, the defect geometry can be more easily identified, which enables the degree of penetration to be more accurately determined using a relationship that is specific to the geometry of the defect.

Figure 13:
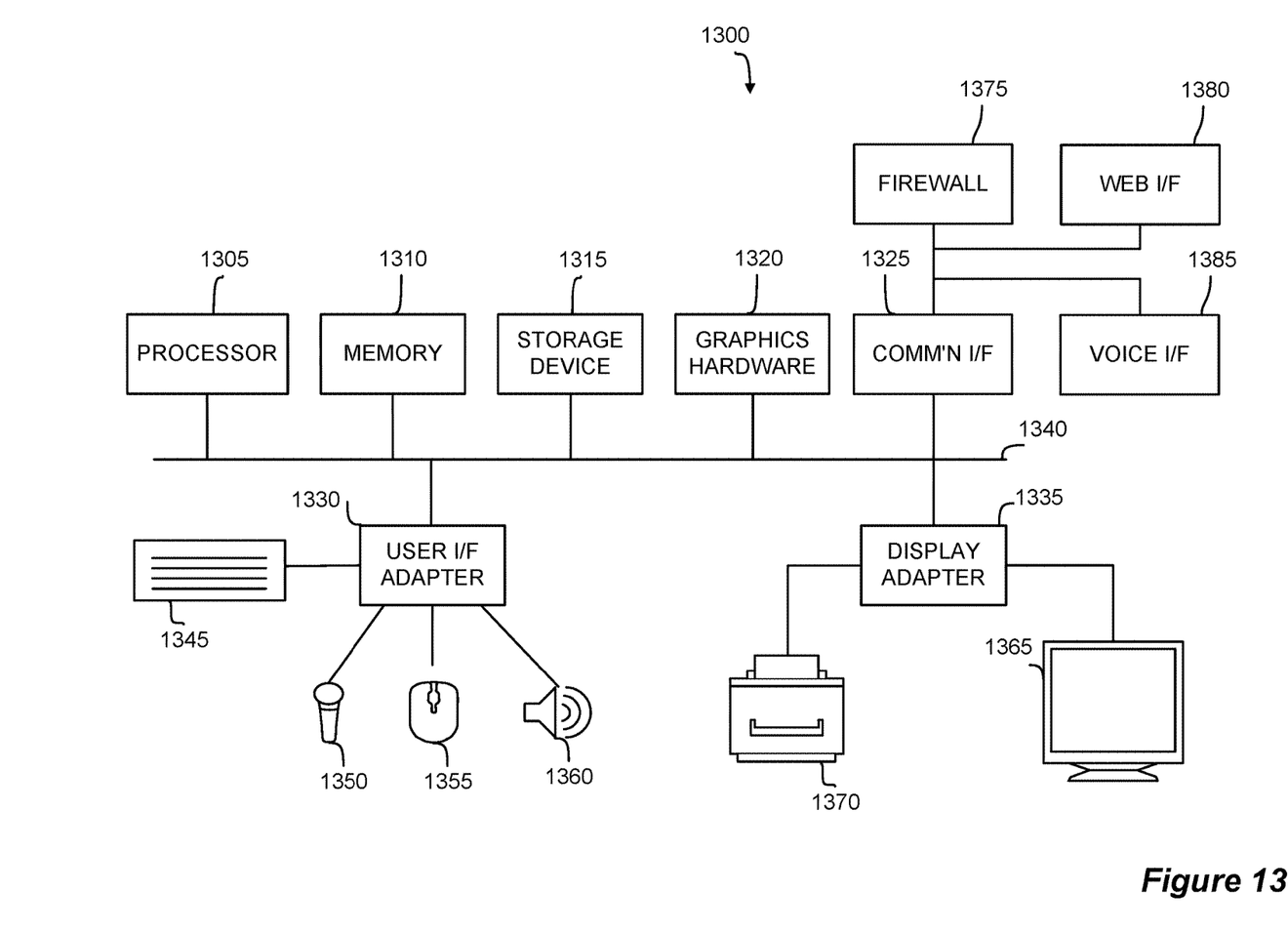
FIG. 13 illustrates a block diagram of a representative system that can execute a portion of the process disclosed in accordance with an aspect of the invention.

FIG. 13 illustrates a representative hardware system 1300. Representative system 1300 includes processor 1305, memory 1310, storage 1315, graphics hardware 1320, communication interface 1325, user interface adapter 1330 and display adapter 1335—all of which may be coupled via system bus or backplane 1340. Memory 1310 may include one or more different types of media (typically solid-state) used by processor 1305 and graphics hardware 1320. For example, memory 1310 may include memory cache, read-only memory (ROM), and/or random access memory (RAM). Storage 1315 may store media, computer program instructions or software, preference information, device profile information, and any other suitable data. Storage 1315 may include one or more non-transitory storage mediums including, for example, magnetic disks (fixed, floppy, and removable) and tape, optical media such as CD-ROMs and digital video disks (DVDs), and semiconductor memory devices such as Electrically Programmable Read-Only Memory (EPROM), Electrically Erasable Programmable Read-Only Memory (EEPROM), and USB or thumb drive. Memory 1310 and storage 1315 may be used to tangibly retain computer program instructions or code organized into one or more modules and written in any desired computer programming language. When executed by processor 1305 and/or graphics processor 1320 such computer program instructions may implement one or more of the processes described herein (e.g., portions of process 600'). Communication interface 1325 may be used to connect system 1300 to a network. Communications directed to system 1300 may be passed through protective firewall 1375. Such communications may be interpreted via web interface 1380 or voice communications interface 1385. Illustrative networks include, but are not limited to: a local network such as a USB network; a business' local area network; or a wide area network such as the Internet. User interface adapter 1330 may be used to connect keyboard 1345, microphone 1350, pointer device 1355, speaker 1360 and other user interface devices such as a touch-pad and/or a touch screen (not shown). Display adapter 1335 may be used to connect display 1365 and printer 1370.

Processor 1305 may include any programmable control device. Processor 1305 may also be implemented as a custom designed circuit that may be embodied in hardware devices such as application specific integrated circuits (ASICs) and field programmable gate arrays (FPGAs). System 1300 may have resident thereon any desired operating system.

While the invention herein disclosed has been described in terms of specific embodiments and applications thereof, numerous modifications and variations could be made thereto by those skilled in the art without departing from the scope of the invention set forth in the claims.

What is claimed is:

1. A method, comprising:
conveying a tool into a wellbore having a casing, wherein the tool comprises a magnet configured to induce a magnetic flux within the casing and wherein the tool further comprises a plurality of corrosion sensors configured to measure magnetic flux;
using the plurality of corrosion sensors to measure magnetic flux at a plurality of locations in the wellbore;
recording a plurality of signals that are each representative of magnetic flux at a location within the wellbore;
arranging the plurality of signals in a matrix that defines an image;
identifying, based on the image, a defect in the casing; and
performing an iterative process comprising:
enhancing a portion of the image in which the defect appears by:
convolving an estimate of the portion of the image by applying a system transfer function to the estimate of the portion of the image, wherein the transfer function is an estimate of how the tool convolves magnetic flux leakage at the defect; and
determining a geometry of the defect from the enhanced portion of the image, wherein
convolving an estimate of the portion of the image generates a blurred image and wherein enhancing the portion of the image further comprises:
subtracting the blurred image from the portion of the image to generate a difference image; and
adding the difference image to the estimate of the portion of the image to generate the enhanced portion of the image, wherein the enhanced portion of the image is used as the estimate of the portion of the image in a subsequent iteration.

2. The method of claim 1, wherein the portion of the image is used as the estimate of the portion of the image for a first iteration.

3. The method of claim 1, wherein the system transfer function is dependent upon the geometry of the defect and the degree of penetration of the defect.

4. The method of claim 3, wherein the system transfer function is selected based on the geometry and the degree of penetration determined during a preceding iteration.

5. The method of claim 3, wherein the system transfer function is selected based upon an assumed geometry and degree of penetration of the defect for a first iteration.

6. The method of claim 1, wherein determining the geometry of the defect from the enhanced portion of the image comprises:
identifying edges of the defect in the enhanced portion of the image; and
determining a first maximum distance between the edges in a longitudinal direction and a second maximum distance between the edges in an azimuthal direction.

7. The method of claim 1, wherein determining the degree of penetration of the defect comprises:
determining a characteristic value of the defect; and
determining the degree of penetration of the defect using a characteristic value-degree of penetration relationship that is specific to the determined geometry.

8. The method of claim 7, wherein the characteristic value-degree of penetration relationship is expressed as an equation.

9. The method of claim 7, wherein the characteristic value-degree of penetration relationship is expressed as a lookup table.

10. A method, comprising:
conveying a tool into a wellbore having a casing, wherein the tool comprises a plurality of corrosion sensors positioned at different locations about the tool;
using the plurality of corrosion sensors to measure magnetic flux at a plurality of locations within the wellbore;
recording a signal representative of magnetic flux from each of the plurality of corrosion sensors at each of a plurality of longitudinal positions;
generating an image from the signals;
identifying a defect in the casing based on the image;
enhancing a portion of the image in which the defect appears to determine a geometry of the defect, wherein enhancing a portion of the image comprises convolving an estimate of the portion of the image by applying a system transfer function to the estimate of the portion of the image, wherein the transfer function is an estimate of how the tool convolves magnetic flux leakage at the defect, wherein
convolving an estimate of the portion of the image generates a blurred image and wherein enhancing the portion of the image further comprises:
subtracting the blurred image from the portion of the image to generate a difference image; and
adding the difference image to the estimate of the portion of the image to generate the enhanced portion of the image, wherein the enhanced portion of the image is used as the estimate of the portion of the image in a subsequent iteration.

11. The method of claim 10, wherein the system transfer function is dependent upon the geometry of the defect and the degree of penetration of the defect.

12. The method of claim 10, wherein determining the degree of penetration of the defect comprises:
determining a characteristic value of the defect; and
determining the degree of penetration of the defect using a characteristic value-degree of penetration relationship that is specific to the determined geometry.

13. The method of claim 12, wherein the characteristic value of the defect is calculated as a second derivative of the recorded signals with respect to a longitudinal position corresponding to the signals.

14. The method of claim 10, wherein the tool comprises a permanent magnet configured to generate magnetic flux within the casing that travels in a longitudinal direction and wherein each of the plurality of corrosion sensors is configured to detect magnetic flux that travels in the longitudinal direction.

15. A system, comprising:
a tool, comprising:
a permanent magnet; and
a plurality of corrosion sensors positioned at different locations about the tool, wherein the tool is configured to record signals representative of magnetic flux from the plurality of corrosion sensors at each of a plurality of longitudinal positions within a wellbore having a casing; and
a non-transitory computer-readable medium having program instructions stored thereon to cause a processor to:
generate an image from the signals;
identify a defect in the casing based on the image;
enhance a portion of the image in which the defect appears to determine a geometry of the defect, wherein enhancing a portion of the image comprises convolving an estimate of the portion of the image by applying a system transfer function to the estimate of the portion of the image, wherein the transfer function is an estimate of how the tool convolves magnetic flux leakage at the defect, wherein the instructions to cause the processor to enhance the portion of the image comprise instructions to cause the processor to iteratively:
convolve an estimate of the portion of the image to generate a blurred image;
subtract the blurred image from the portion of the image to generate a difference image; and
add the difference image to the estimate of the portion of the image to generate the enhanced portion of the image, wherein the enhanced portion of the image is used as the estimate of the portion of the image in a subsequent iteration.

16. The method of claim 1, further comprising determining a degree of penetration of the defect based on the determined geometry.

17. The method of claim 10, further comprising determining a degree of penetration of the defect based on the determined geometry.

18. The system of claim 15, wherein the program instructions further cause the processor to determine a degree of penetration of the defect based on the determined geometry.

* * * * *